United States Patent [19]

Valla et al.

[11] Patent Number: 5,300,508

[45] Date of Patent: Apr. 5, 1994

[54] METHOD FOR INTERCEPTING ACTIVATED SPECIES OF DIOXYGEN

[75] Inventors: Alain Valla, Drancy; Michel Giraud, Etampes; Marc Bazin, Le Mee; René Santus, Crepy en Valois, all of France

[73] Assignee: Centre National de la Recherche Scientifique, Paris, France

[21] Appl. No.: 809,515

[22] PCT Filed: Jun. 5, 1990

[86] PCT No.: PCT/FR90/00395

§ 371 Date: Jan. 31, 1992

§ 102(e) Date: Jan. 31, 1992

[87] PCT Pub. No.: WO90/15051

PCT Pub. Date: Dec. 13, 1990

[30] Foreign Application Priority Data

Jun. 6, 1989 [FR] France ............ 89 07475

[51] Int. Cl.$^5$ ............ A61K 31/40; A61K 7/00; C07D 207/327; C07D 403/04; C07D 473/34

[52] U.S. Cl. ............ 514/258; 514/266; 514/269; 514/274; 514/397; 514/427; 544/280; 544/301; 544/316; 548/314.7; 548/557; 548/562

[58] Field of Search ............ 548/562, 557, 314.7; 514/258, 266, 269, 274, 397, 427; 544/280, 301, 316

[56] References Cited

U.S. PATENT DOCUMENTS 3,869,554  3/1975  Pittet et al. ............ 548/562 X
4,150,224  4/1979  Nudelman et al. ............ 548/562 X
4,563,477  1/1986  Maldonado et al. ............ 548/562 X

FOREIGN PATENT DOCUMENTS 1938904  2/1970  Fed. Rep. of Germany ...... 548/562
2647368  5/1977  Fed. Rep. of Germany ...... 548/562

(List continued on next page.)

OTHER PUBLICATIONS

Hayashi et al, Chemical Abstracts, vol. 91, #5201e (1979).

(List continued on next page.)

Primary Examiner—Floyd D. Higel
Attorney, Agent, or Firm—Nixon & Vanderhye

[57] ABSTRACT

A method for intercepting an activated species of dioxygen by administering an N-substituted pyrrole derivative having the formula:

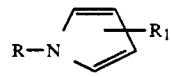

in which:

R is an amino acid derivative, a non-protein peptide, an amino sugar processing a free primary amino group, a purine bases which is substituted, at position 9 by alkyl groups, or a pyrimidine bases possessing a free primary amino group, wherein the pyrimidine bases are substituted by at least one SH group; $R_1$ represents one or more substituents, identical or different and are a hydrogen, an alkyl radical containing from 1 to 6 carbon atoms, a primary amino radical, a secondary amino radical NHB, or a tertiary amino radical—N(B,B'), wherein B and B', identical or different represent an alkyl group of 1 to 6 carbon atoms, a SH or SB radical, wherein B is defined above, a —CH$_2$OH, —CH(B)OH, —C(B,B')OH radical or the corresponding esters and ethers, a cyclic radical of 3 to 6 carbon atoms or an oxygen, nitrogen or sulfur containing heterocycle such as furan, pyrrole or thiophene, or their salts with metal ions or amine complexes, esters of formula —COOR$_2$, wherein R$_2$ is an alkyl radical of 1 to 3 carbon atoms, amides of the formula COR$_3$ wherein R$_3$ is a primary, secondary and/or tertiary amine and wherein R$_3$ is a secondary or tertiary amine said primary or tertiary amine is substituted by an alkyl group or alcohol of 1 to 4 carbon atoms or their complexes with physiologically acceptable salts wherein said N-substituted pyrrole derivatives are racemates or are optically active isomers, with the proviso that $R_1$ is not hydrogen when R is a derivative selected from the group consisting of glycine, leucine, phenylalanine, tyrosine, serine and glutamic acid.

12 Claims, No Drawings

FOREIGN PATENT DOCUMENTS

| | | | |
|---|---|---|---|
| 2492374 | 4/1982 | France | 548/562 |
| 2526793 | 11/1983 | France | 548/562 |
| 2551063 | 3/1985 | France | 548/562 |
| 53-81635 | 7/1978 | Japan | 548/562 |

OTHER PUBLICATIONS

Ho et al, J. Med. Chem., vol. 13, pp. 1022, 1023 (1970).

Kashima et al I, Heterocycles, vol. 27, pp. 1727 to 1730 (1988).

Kashima et al II, J. Chem. Research, S, vol. of (1988), pp. 62, 63.

Massa et al, Il Farmaco Ed. Sc., vol. 38, pp. 90 to 100 (1983).

Valla et al, Eur. J. Med. Chem., vol. 13, pp. 93 to 96 (1978).

Youssefyeh et al, J. Heterocyclic Chem., vol. 8, pp. 33 to 35 (1971).

Chemical Abstracts, vol. 86, No. 23, Jun. 6, 1977, Columbus, Ohio, US p. 481, No. 170600p; A. R. Katritzky.

Collection of Czechoslovak Chemical Communications, vol. 33, No. 3, 1968, pp. 1307–1314, Prague, CS; J. Gloede et al.

METHOD FOR INTERCEPTING ACTIVATED SPECIES OF DIOXYGEN

The invention relates to interceptors of activated species of dioxygen, their preparation process and the pharmaceutical and cosmetic compounds containing them.

Activated species of dioxygen, plus especially singlet oxygen($^1O_2$), the superoxide radical ion ($O^{2\cdot}$), the hydroxyl radical ($OH^1$), alkoperoxyl radicals ($AOO^1$) and alkoxyl radicals ($AO\cdot$), in which A represents an alcoyl (alkyl) grouping, are pathogenic entities relative to the cell.

These activated species play a fundamental role in the development or aggravation of numerous illnesses such as cancer, infarction, emphysema, arteriosclerosis, and rheumatoid arthritis.

Further, these activated species are involved in the aging processes of organs, in particular of the skin, whether these processes are natural or whether they result from luminous radiation.

Up to now, several types of interceptors of activated species of dioxygen have been used in medical practice or in cosmetology. Those most commonly used are vitamins or their derivates, in particular ascorbic acid and vitamin E, oxidants derived from phenol (tert-butyl hydroxytoluene and tert-butyl hydroxyanisole), thiol derivates such as cysteine and its derivates, dismutase superoxide and the carotenoids.

However, these substances are not totally satisfactory as interceptors against activated species of dioxygen. Indeed, some of them react only with a single activated species, or are unstable or even prove inappropriate because of their hydrophilic or hydrophobic or photo-sensitizing nature.

The inventors have searched for products able to react more efficiently against the activated species of oxygen involved in the aging processes of organs and of cells and in diverse pathologies associated with the involvement of these activated species of dioxygen.

They have thus confirmed that the substitution of the nitrogen atom of pyrrol derivates by groups involved in cellular metabolism gives them, in particular, advantageous properties as interceptors relative to activated species of dioxygen.

The object of the invention is new pyrrol derivates having properties of interceptors of activated species of dioxygen. The object also is compounds containing these pyrrol derivates. The object of the invention is also their preparation process and pharmaceutical compounds containing them.

The invention thus relates to new pyrrol derivates that fulfill the following characteristics:
- they react with activated species of dioxygen, in particular with singlet oxygen, OH radicals, free radicals of the inorganic radical type. Toward these radicals, they have an activity distinguished by a bimolecular reaction rate constant on the order of $10^9 M^{-1}$. Some of them react also with the superoxide ion formed during cellular photooxidation or autooxidation reactions,
- they are stable in darkness and in light under the following conditions: in buffered, neutral solution and in darkness, they are stable practically indefinitely at 4° C. (more than a month), and at room temperature, some of them exhibit an equivalent stability.
- they have a partition coefficient between the lipophilic phase and the hydrophilic phase that varies between 2 and 50 for the conventional water-octanol mixture,
- they are stable in the usual organic solvents such as D.M.S.O., ethanol, in particular at room temperature,
- they are physiologically acceptable for human fibroblasts,
- they are not sensitive to the action of cellular hydrolases and esterases.

Derivates particularly adapted to achieving the invention are N-substituted pyrrol derivates corresponding to following formula (I):

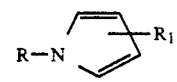

in which:
R is a physiologically acceptable constituent, able to penetrate into cells, insensitive to the action of cellular hydrolases and esterases, this grouping being in particular a derivate of amino acids, of biologically desirable nonproteinic peptides, of osamines having a free primary amine grouping, of purine bases, if necessary substituted in position 9 by groupings other than phenyl, for example by alkyl groupings, or of pyrimidic bases having a free primary amine grouping, pyrimidic bases being substituted by at least one SH group, R1 represents one or more identical or different substituents selected from among a hydrogen or an alcoyl radical comprising 1 to 6 carbon atoms, a primary, secondary —NHB, or tertiary —N(B,B') amine radical, with B and B' identical or different and representing an alcoyl group of 1 to 6 carbon atoms, an SH or SB radical, B being as defined above, a —CH$_2$H, —CH(B)OH, —C(B,B')OH radical or corresponding ethers and esters, a cyclic radical of 3 to 6 carbon atoms or an oxygenous, nitrogenous, or sulfurous heterocycle, such as furan, pyrrol or thiophene, and their salts, in particular salts that act as carboxylics of radicals R with metallic ions or physiologically acceptable amines, their esters of formula —COOR$_2$, R$_2$ being an alkyl radical, in particular with 1 to 3 C atoms, COR$_3$ amides with R$_3$ being a primary, secondary and/or tertiary amine, in the last two cases substituted by an alcoyl or alcohol group with 1 to 4 carbon atoms and their complexes with physiologically acceptable metals, these N-substituted pyrrol derivates being in the racemic form or in the form of optically active isomers provided that R$_1$ is different from hydrogen when R is a derivate of glycine, leucine, phenylalanine, tyrosine, serine, or glutamic acid.

It will be observed that the compounds from which R is derived comprise a free NH$_2$ group acting to form the network of the pyrrol cycle.

Preferably, the pyrrol cycle comprises two substituents R$_1$ according to the preceding definitions. These substituents occupy positions 2,3; 2,4; 2,5; or 3,4 in the pyrrol cycle.

In a variant, the pyrrol cycle of derivates of the invention comprise three substituents R$_1$, identical or different, in position 2, 3, 4 or 2, 3, 5.

This cycle can also comprise four substituents, according to yet another variant.

Particularly desirable $R_2$ substituents are: $CH_3$, $C_2H_5$, $CH_2CH_2CH_3$, $CH(CH_3)_2$.

Particularly desirable $R_3$ substituents are: $NH_2$, $NH(CH_3)$, $N(CH_3)_2$, $N(C_2H_5)_2$, $NHCH_2CH_2CH_3$, $NHCH(CH_3)_2$, $NHCH_2CH_2OH$, $NHCH_2CH_2N(C_2H_5)_2$.

The compounds of the invention offer, in an extremely advantageous way for achieving the invention, an increased reactivity relative to diverse activated species of dioxygen and relative to slightly oxidizing inorganic radicals such as $Br_2\cdot$ and $SCN_2\cdot$.

These compounds are thus particularly useful in fighting against pathologies involving reactions with said activated species of dioxygen. The term "pathologies" encompasses simultaneously illnesses in which activated species of dioxygen are involved and superficial manifestations, e.g., at the level of the skin, in particular solar erythema and edema caused by cellular reactions involving activated species of dioxygen. In other words, the compounds of the invention are active relative to entities that are pathogenic toward cells, consisting of activated species of dioxygen.

A first preferred group of compounds according to the invention is the group of pyrrol derivates, characterized above in that R is a derivate of amino acids, in particular of alanine, histidine, tryptophan, cysteine, lysine, ornithine, or tyrosine.

Another preferred group of compounds according to the invention comprises pyrrol derivates characterized in that R is a derivate of a nonproteinic peptide, e.g., of glutathione, or of carnosine, of homocarnosine, or of a hormonal peptide.

In an advantageous way for achieving the invention, the nonproteinic peptides have the capacity to break through enzymatic cellular barriers.

The case of glutathione is particularly interesting since, in reduced form, besides its role as a good interceptor of radicals, it is involved in the enzymatic cascade leading to $PGE_2$ prostaglandins.

A third group of compounds that are advantageous for achieving the invention comprises derivates characterized in that R comes from a purine or pyrimidic base selected in particular from among adenine, guanine or cytosine.

These compounds make it possible to amplify antioxidizing properties.

Another particularly desirable property of these constituents results from the fact that they are built from biologically desirable molecules, i.e., necessary for cellular metabolism.

Other compounds that fulfill the preceding characteristics can be characterized in that they are positively charged and preferably in that they involve pyrrol derivates of polyamines or of basic amino acids such as arginine or lysine.

Other preferred pyrrol derivates are negatively charged derivates, preferably pyrrol derivates of glutamine or of asparagine.

Advantageously, constituents such as Lys-Cys-Pyr, Lys-Ala-Pyr, Lys-Trp-Pyr (in which Lys=lysine, Cys=cysteine, Ala=alanine, Trp=tryptophan, Pyr=pyrrol) can be used to achieve the invention.

The derivates containing residual cysteine are particularly preferred.

In an advantageous embodiment of the invention, the derivates corresponding to the general formula above are such that there are two substituents $R_1$ that are placed in position 2 and 5 respectively of the pyrrol cycle. Particularly desirable compounds are pyrrol derivates for which $R_1$ are alcoyl groupings, more specifically, methyl.

The pyrrol derivates of the invention can also form complexes with metal ions. Preferred ions are $Cu^{++}$ or $Fe^{++}$. According to a preferred aspect, the pyrrol derivates obtained from alanine or histidine constitute good complexing agents of copper ions.

The salts of derivates and complexes of the invention also are part of the scope of the latter.

Among the N-substituted pyrrol derivates according to the invention, certain ones feature optical activity. These, for example, are the compounds obtained from amino acids, peptides, osamines. These pyrrol derivates are advantageously obtained from amino acids, peptides, osamines having natural configuration or from their optical isomers.

Thus, for achieving the invention, use of either a racemic mixture or of the optically active isomers will be selected depending on the effect sought.

According to another aspect, the invention also has the object of using, for the production of a compound exhibiting activity as an interceptor of activated species of dioxygen, derivates of formula I in which R is a physiologically acceptable chemical grouping, able to penetrate into cells, insensitive to the action of cellular hydrolases and esterases, this grouping being in particular a derivate of amino acids, of biologically desirable nonproteinic peptides, of osamines having a free primary amine grouping, of purine bases, if necessary substituted in position 9 by groupings other than phenyl, for example by alkyl groupings, or of pyrimidic bases having a free primary amine grouping, pyrimidic bases being substituted by at least one SH group, $R_1$ represents one or more identical or different substituents selected from among an alcoyl grouping comprising 1 to 6 carbon atoms, a primary, secondary —NHB, or tertiary N(B,B') amine grouping, with B and B' identical or different and representing an alcoyl group of 1 to 6 carbon atoms, an SH or SB group, B being as defined above, or a —CH$_2$OH, —CH(B)OH, —C(B,B')OH group or corresponding ethers and esters, a cyclic residue of 3 to 6 carbon atoms or an oxygenous, nitrogenous, or sulfurous heterocycle, such as furan, pyrrol or thiophene, and their salts, in particular salts that act as carboxylics of radicals R with metallic ions or physiologically acceptable amines, their esters of formula —COOR$_2$, R$_2$ being an alkyl radical, in particular with 1 to 3 C atoms, COR$_3$ amides with R$_3$ being a primary, secondary and/or tertiary amine, in the last two cases substituted by an alcoyl or alcohol group with 1 to 4 carbon atoms and their complexes with physiologically acceptable metals, these N-substituted pyrrol derivates being in the racemic form or in the form of optically active isomers.

These derivates are used for the production of a medicine useful, in particular, in the treatment of cancer, infarction, emphysema, arteriosclerosis, rheumatoid arthritis and other pathologies mentioned above. By way of example, the pharmaceutical compounds of the invention can be administered by oral, intravenous means according to the doses usually used in the treatment of the above pathologies.

The antiinflammatory properties of the products can be tested according to all methods allowing the study of antiinflammatory properties of medicines:
  inhibition of edema and solar erythema,
  inhibition of edema and erythema with $LTB_4$ or with arachidonic acid or with other phorbol derivates,
  inhibition of edema and erythema with carrageenin,
  inhibition of the contraction of the smooth muscles (intestines, bronchi) under the action of various pro-inflammatory agents.

The properties of the pyrrol derivates of the invention also make it possible to apply them in the formulation of cosmetic compounds, characterized in that the pyrrol derivate(s) are present in an amount on the order of 0.1% to 2% by volume, in association with a cosmetic vehicle selected, for example, from among the liposomes, cyclodextrin, the phytosomes or other vehicles that are part of the composition of pomades, gels, lotions, creams or other forms of conventional administration.

These products can then be used in a topical and local fashion to fight against superficial manifestations of the aging of the skin or against cutaneous manifestations due to photo-induced reactions.

Placing the active substance into "solution" to achieve the formulation can be performed in several ways:
  in the form of a free acid,
  in the form of an acid salt,
  by the intermediary of a functional grouping present in the aliphatic chain or at an aromatic ring: acid salt, quaternary ammonium salt, salts derived by an activity of alcohol or thiol or phenol . . .

Another application of the pyrrol derivates according to the invention is that of antioxidizing agents in agroalimentary products.

The derivates of the invention can also be used as biological reagents.

The object of the invention is thus compounds exhibiting, in particular, an activity as an interceptor of activated species of dioxygen, comprising at least one pyrrol derivate corresponding to the criteria given in the preceding pages.

Advantageously, these compounds exhibit multifunctional properties, i.e., relative to several activated forms of dioxygen.

Preferably, e.g., the compound thus defined is bifunctional and reacts, e.g., with $^1O_2$ and $O_2^-$ or $^1O_2$ and OH· or is trifunctional and reacts, e.g., with $^1O_2$, OH·, and $O_2^-$.

The in vitro properties of the different interceptors of activated species of dioxygen can be tested by the following methods:
  the first method makes it possible to judge the effectiveness of pyrrol derivates as inhibitors of photobiological effects involving $^1O_2$ and the lipidic peroxides,
  the second makes it possible to test their value as inhibitors of cellular autooxidation processes.

By microspectrofluorometry on human fibroblasts in a monolayer culture, the capacity of the pyrrol derivates to inhibit the formation, by photosensitization, of fluorescent pigments of the lipofuscin type was determined. These pigments result from the formation of Schiff bases between the aldehydes (in particular malonaldehyde or hydroxy-4-nonenal) resulting from the peroxidation of lipids by the $^1O_2$ produced, by the irradiation of a single cell, after a preincubation with a photosensitizing agent. Then it is suitable, as previously shown, by Morliers et al. (Photochem., Photobiol. 46, 183-91 (1987)) to study the kinetics of the appearance of these fluorescent pigments (their maximum fluorescence is around 470 nm) within the cell, in the presence and absence of inhibitors.

To study the effect of pyrrol derivates on cellular autoperoxidation, human fibroblasts are incubated at 37° C. for one night with $Fe^{2+}$ ions, which induces peroxidation of cellular lipids. The latter will be measured by the well-known thiobarbituric acid (TBA) test using detection by fluorescence after extraction with 1-butanol of the compounds resulting from TBA-aldehyde coupling. The effect of these derivates on the ability of cells to synthesize DNA after peroxidation in the presence of $Fe^{2+}$ is also measured.

These tests have made it possible to reveal the properties of the pyrrol derivates of the invention as interceptors of activated species of dioxygen. The study of the above compounds has shown that they are not toxic. They are thus advantageously used in the treatment of pathologies involving chemical reactions with activated species of dioxygen. Involved in particular are the treatment of porphyrias, of the otolaryngology area, of asthmatic, inflammatory, atheromatous, or allergic illnesses, anticancer prevention, immunomodulator or radioprotection treatments.

Thus pharmaceutical compounds comprising an effective amount of at least one pyrrol derivate corresponding to the above definitions, in association with an acceptable pharmaceutical vehicle, enter into the scope of the invention.

The object of the invention is also a preparation process for the derivates corresponding to formula I and defined above in the scope of their use.

According to this process, an amino derivate of formula (II)$RNH_2$ is reacted with a diketone of formula (III)$R_1CO\ (CHR_1)_2$—CO—$R_1$, which produces a pyrrol derivate of formula I, R and $R_1$ being as defined above.

The condensation step among the derivates of formulas II and III is advantageously performed in the presence of an excess of diketone, on the order of 5 to 10% with respect to the stoichiometry of the reaction when a solvent other than diketone itself is used.

To accelerate the condensation reaction, a temperature higher than room temperature is used, advantageously above 100° C., in particular between 110° C. and 150° C.

The synthesis reaction is advantageously performed under a gas stream, in particular under a nitrogen stream.

The product thus obtained is washed, precipitated and the precipitate is then rewashed and purified in particular with HPLC.

The reaction environment used consists of diketone and amine, possible in the presence of acetic acid, or of a dipolar aprotic solvent (such as dimethyl sulfoxide, dimethyl formamide, hexamethylphosphorous triamide). In the examples shown below, hexanedione-2,5 was used as diketone-1,4, thus producing derivates of dimethyl-2,5 pyrrol. The yield is generally satisfactory (above 50%).

The above arrangements make it possible to mitigate the insolubility of some of the amino derivates in the usual organic solvents.

The study of the reactivity of the pyrrol derivates with different activated species of dioxygen and with slightly oxidizing radicals such as $Br_2^-$, $SCN_2^-$ has shown the desirability of these pyrrol derivates as interceptors of activated species of dioxygen. Further, the pyrrol derivates of the invention are stable.

Particular properties of the pyrrol derivates adapted to achieving the invention will come out from the following examples.

EXAMPLE 1

Synthesis and Characterization of Pyrrol Derivates (these derivates are designated below by codes for easier reading).

I—Glycine pyrrol (COONa) designated by GlyPyr (COONa)

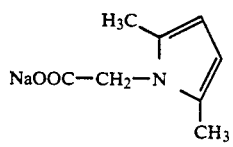

970 mg of glycine (sodium salt, $10^{-2}$ mol), about 1.2 g ($-$)$10^{-2}$ mol) of acetonylacetone and 10 ml of dimethyl sulfoxide were heated for about 3 mn at a temperature of 110°-120° C. under a nitrogen stream. After cooling to room temperature, the product was washed twice with 20 ml of pentane and the pyrrol was precipitated with a minimum of cold ethyl acetate. The white powder was dried and washed with a minimum of cold ethyl acetate. The yield obtained was about 85%. The final product was characterized by its physico-chemical properties and in particular by its IR, UV absorption spectra, its NMR$^1$H.

UV (water): 212 ($\epsilon = 8000$); IR (KBr) 1625 (TF); 1605 (TF); 1320 (F); 740 (F).

$^1$H-NMR (D$_2$O) (H$_2$O:4.6 ref.int.):CH-=-s:5.63; CH$_3$-=- s: 1.82; CH$_2$ s: 4.21.

II—alanine pyrrol (COONa) :AlsPyr (COONa)

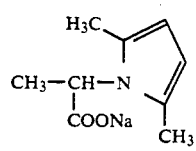

The synthesis was performed according to the same process as the one described in I by condensation of alanine with acetonylacetone. After washings with pentane, pyrrol was precipitated with a minimum amount of dry ether. Then filtering and washing were performed with a minimum amount of cold ethyl acetate. The final product is a white powder obtained with about an 80% yield.

The product is characterized as follows: UV (phosphate buffer, 50 mmol: pH: 7): 210 nm ($\epsilon = 7900$); IR (KBr): 1594 (TF); 1407 (TF); 1300 (F); 757 (F).

$^1$H-NMR (D$_2$O) H$_2$O: 4.6 ref.int.): CH-=-s:5.76; CH$_3$-=-s:2.15; CH—CH$_3$q:4.74 (J=7.35Hz); CH$_3$—CHd:1.48 (J=7.35 Hz).

III—Phenylalanine pyrrol: PhePyr

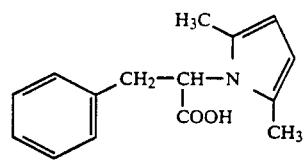

1.65 g ($10^{-2}$ mol) of phenylalanine and 5 ml of acetonylacetone were heated under a nitrogen stream to a temperature of about 130° C., until a clear solution was obtained ($-$5-10 mn). After cooling to room temperature, the pyrrol was washed twice with 50 ml of pentane and dried. The product obtained was washed with the minimum of dry ether. An almost white powder was recovered with a yield of about 80%.

The characteristics of the product are the following:

It decomposes starting at 160° C., melting point UV (H$_2$O): 207 nm ($\epsilon = 8000$); IR (KBr): 1715 (TF); 1400 (TF); 1395 (TF); 760 (TF); 700 (TF)

$^1$H-NMR (CDCl$_3$) CH-=- s:5.75; CH$_3$-=-s:2.00; C$_6$H$_5$-m: 6.80-7.00 (2pr.), m:7.12-7.24 (3pr.); CH—CH$_2$ ABX system mass 4.77-5.0; CH$_2$CH ABXm 3.05-3.70; ABX calculated: $\delta$HA=3.55 ppm; $\delta$HB=3.22 ppm; $\delta$HX=4.86; J (A-B)=14 Hz: K (A-X)=4.80 Hz; J (B-X)=9.9 Hz.

IV—Pyrimidine pyrrol: PyPyr

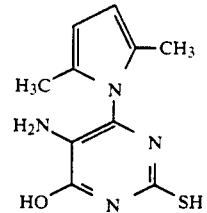

1.58 g ($10^{-2}$ mol) of diamino-5,6-2-thiouracil in the minimum of hexamethylphosphorous triamide was dissolved under a nitrogen stream at about 50° C. 1.2 g ($-10^{-2}$ mol) of acetonylacetone was added and the temperature was raised to about 130° C. ($-$10-15 nm). It was left to return to room temperature and washed twice with 30 ml of pentane. The pyrrol was precipitated by dry dichloromethane. Then it was dried and washed with dichloromethane. The product is obtained with a yield of about 85%.

Its characteristics are the following: Melting point F greater than 260° C., UV (phosphate buffer, 50 mmol at pH: 7 :284 (e=3400); 260 ($\epsilon = 2600$); 210 ($\epsilon = 7600$); IR (KHr): 3400 (F); 3275 (F); 1690 (TF); 1605 (TF); 1556 (TF); 1405 (TF); 1195 (TF); 1161 (TF); 991 (TF); 971 (TF); 772 (TF); 748 (TF)

$^1$H-NMR (DMSO d-6): CH-=- s;5.74: CH$_3$-=-s:1.91; mass 236; 179; 135; 92.

V—adenine pyrrol: AdePyr

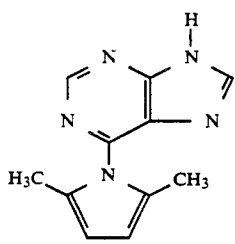

1.55 g ($10^{-2}$ mol) of adenine and 1.5 ml of acetonylacetone were heated under a nitrogen stream to a temperature of about 140° C., until the mixture becomes clear (~5-10mn). After cooling, it was washed twice with 50 ml of pentane and the pyrrol was precipitated with a minimum amount of dry ether. Then it was dried and washed with the minimum of dry ether. The product is obtained with a yield of about 80%.

Its characteristics are the following: Melting point $F_{(dec)}$250° C., UV ($C_2H_5OH$): 280 (8600); 210 (9000); IR (KBr): 1615 (TF); 1590 (TF); 1410 (TF); 1315 (TF); 1215 (TF); 765 (TF); 645 (TF)

$^1$H-NMR ($CD_3COCD_3$): CH-=-s:5.88; $CH_3$-=-s:2.15; N—CH—NH s:8.51; N=CH—N=CH—N s;8.88.

VI—Histidine pyrrol: HisPyr 1.55 g ($10^{-2}$ mol) of histidine, 1.2 g (~$10^{-2}$ mol) of acetonylacetone and 5 ml of dimethyl sulfoxide were heated, under a nitrogen stream, to a temperature of about 125° C. until the reaction mixture becomes clear (~10mn). Then it was cooled and washed twice with 30 ml of pentane. The product, beginning to crystallize, was precipitated totally by 20 ml of dry ether. Then it was dried and washed with a minimum amount of dry ether. The product obtained has a yield of about 80%.

It is characterized by the following properties: Melting point F: 173° C.

UV (phosphate buffer, 50 mmol at pH:7:210 ($\epsilon$=9800); IR (KBr): 3455 (F); 3130 (F); 1630ep1595 (TF); 1404ep1374 (TF); 1024 (F); 751 (F).

$^1$H-NMR (DMSO d-6/N=CH—NH m: 7.62; HN—CH=C m :6.41; CH=C—$CH_3$s: 5.51; $CH_3$ s: 2.00; CH—$CH_2$ABX m: 4.98-4.93; $CH_2$—CH ABX m: 3.7-3.0; ABX: calculated: $\delta HA$=3.37 ppm; $\delta HB$=3.04 ppm; $\delta HX$=4.95; J (A-B)=15 Hz; J (A-X)=5.3 Hz; J (B-X)=10 Hz mass: 233; 215; 189; 135; 120; 108; 94.

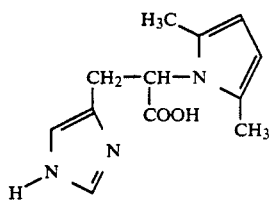

VII—Homocarnosine-pyrrol: HcarPyr 1.2 g ($0.5.10^{-2}$ mol) of homocarnosine and 750 mg (~$0\ 5.10^{-2}$ mol) of acetonylacetone in 15 ml of acetic acid were brought to boil in 3 mn under a nitrogen stream. The acetic acid was distilled under reduced pressure, then the reaction mixture was washed twice with 20 ml of pentane and the pyrrol was precipitated by ether (~30 ml). A pink, almost white powder was obtained with a yield close to 85%.

The characteristics of the product are the following: It decomposes starting at 140° C..

UV (phosphate buffer, 50 mmol at pH:7: 210 ($\epsilon$=11000) IR (KBr): 3315 (F); 1651 (TF); 1411 (TF); 1300 (F); 845 (F); 750 (F); 633 (F).

$^1$H-NMR ($D_2O$) N=CH—NH d: 8.40 (J=1.4 Hz); HN—CH—=C m :7.07; $CH_2$—C=O m: 3.59-3.50; $CH_2$—N m: 2.13-2.04; $CH_2$—$CH_2$ m: 1.67-1.57; CH—$CH_3$ s:4.6; $CH_3$ s: 1.96; CH—$CH_2$: ABX system. Two multiplets (6.61-5.89 and 6.02-5.31); ABX calculated: $\delta HA$=3.08 ppm; $\delta HB$=2.88 ppm; $\delta HX$=6.25: J (A-B)=15.25 Hz; J (A-X)=4.9 Hz; J (B-X)=9 Hz; Mass: 381; 210; 181; 158; 135; 120; 108; 94

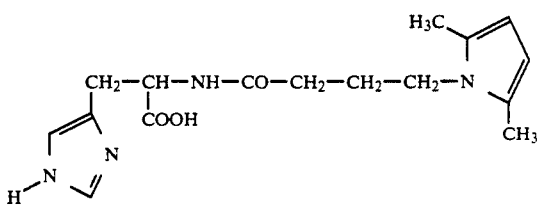

VIII—Carnosine-pyrrol CarPyr 1.08 g ($0.5.10^{-2}$ mol) of carnosine and 750 mg (~$0.5.10^{-1}$ mol) of acetonylacetone in 15 ml of acetic acid were treated for 3 mn to boiling. As previously, pyrrol was isolated in the form of a pink, almost white powder with a yield close to 85%.

The characteristics of the final product are: Decomposition starting at 150° C.

UV (phosphate buffer, 50 mmol a pH:7: 210 ($\epsilon$=11000); IR (KBr): 3280 (F); 1660 (TF); 1650ep1620 (TF); 1580ep1565 (TF); 1540 (F): 1407 (F); 1300 (F); 1245 (F); 845 (F); 755 (F); 630 (F);

$^1$H-NMR (DMSO d-6): NH—CH=N d: 7.62 (J=1.1 Hz); HN—CH=C m: 6.77; O=C—$CH_2$t: 2.37 (J=7.6 Hz); $CH_2$—N t: 3.85 (J=7.6 Hz); CH—$CH_3$s: 5.56; $CH_3$ S/2.11; $CH_2$CH ABX m: 2.77-2.97; CH-$CH_2$; ABX m: 4.38-4.45; ABX calculated: $\delta HA$=2.94 ppm; $\delta HB$=2.81 ppm; $\delta HX$=4.41; J (A-B)=14.8 Hz; J (A-X)=5.8 Hz; J (B-X)=8.5 Hz

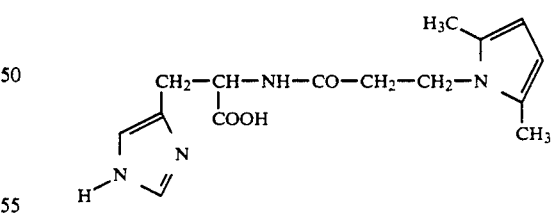

EXAMPLE 2

Study of the reactivity of N-substituted pyrrol derivates with singulet oxygen.

The bimolecular reaction rate constants (k: ($M^{-1}s^{-1}$)) of singulet oxygen with N-substituted pyrrols obtained from precursors of biological macromolecules (amino acids, purine and pyrimidic bases, osamines and their combinations) were measured. The reactivity was tested relative to $^1O_2$ at pH 7 in buffered aqueous solution (the measurement of the rate constant was performed according to the method of comparison explained by GIRAUD et al (J. Chem. Soc. Chem. Comm., (1982), 1146-8).

The results of table 1 relate to the following compounds: Pyr=dimethyl-2,5-pyrrol; Ala=alanine: His=histidine: Trp =tryptophan; Cys=cysteine; Lys=lysine; Ade=adenine; Car=carnosine; Hcar=-homocarnosine.

The numeral 0 appearing in all the tables given below signifies that no reactivity was detected under the experimental conditions selected.

TABLE 1

| Substrat | Ala | AlaPyr | His | HisPyr | Trp | TrpPyr |
|---|---|---|---|---|---|---|
| k | ~0 | $3.10^8$ | $4.4.10^7$ | $1.3.10^8$ | $5.8.10^7$ | $1.6.10^8$ |
| Substrat | Lys | LysPyr | Cys | CysPyr | Py | PyPyr |
| k | 0 | $2.5.10^8$ | $8.9.10^6$ | $1.4.10^8$ | $3.10^8$ | $1.2.10^8$ |
| Substrat | Ade | AdePyr | Car | CarPyr | Hear | HearPyr |
| k | ~0 | $2.10^8$ | $5.10^7$ | $5.7.10^8$ | $6.6.10^7$ | $8.2.10^8$ |

Key:
[substrat] substrate

Table 1 shows, with several examples, that the molecules thus obtained have a considerably increased reactivity relative to $^1O_2$ compared to the corresponding amino acid or the corresponding purine or pyrimidic bases, in particular for Cys and especially for Ala, which does not react with $^1O_2$. at physiological pH.

EXAMPLE 3

Study of the reactivity of pyrrol derivates and their metal complexes with $O_2$·, OH-radicals and with slightly oxidizing radicals ($Br_2^-$ and $SCN_2^-$).

Table 2 below shows, with several selected examples, the results of measurements performed by pulsed radiolysis (according to the technique explained in US Department of Commerce NBS document 59, 1977) relating to the reactivity of these derivates with either very oxidizing radicals (OH.) or more slightly oxidizing radicals ($Br_2^-$, $SCN_2^-$). These latter being commonly used to test reactivity relative to oxidizing radicals, it is confirmed that the synthetic products exhibit great reactivity with OH-. radicals. In fact, the reaction rate constants are practically those of reactions controlled by diffusion, while this is not always the case of base compounds (see, e.g., AlaPyr and LysPyr compared, respectively to alanine and lysine). The contrast is still greater where reactivity with $Br_2^-$ and $SCN_2^-$ radicals are concerned, since all the derivates react very easily with the latter while, and this is directly comparable with the results obtained for the interception of singulet oxygen, certain parent products are not reactive (alanine, lysine).

These results thus show the importance of the dimethylpyrrol grouping for the amplification of "antioxidizing" properties. On the other hand, the comparison of the reactivities of LysPyr and of AlaPyr relative to negatively charged radicals underlines, in the case of LysPyr, an increase in reactivity tied to the positive charge of the Lysyle [sic] grouping. Thus the reactivity of these derivates can be modulated by using compounds such as Lys-Cys-Pyr, Lys-Ala-Pyr, Lys-Trp-Pyr.

TABLE 2

| Radicaux Dérivés | OH- | $Br_2^-$. | $SCN_2^-$. |
|---|---|---|---|
| AlaPyr | $5.10^9$ | $7,5.10^8$ | $8.10^8$ |
| CysPyr | $4.10^9$ | $4.10^8$ | $3,3.10^8$ |
| LysPyr | $8.10^9$ | $1,3.10^9$ | $1,3.10^9$ |

TABLE 2-continued

| Radicaux Dérivés | OH- | $Br_2^-$. | $SCN_2^-$. |
|---|---|---|---|
| TrpPyr | $8.10^9$ | $7.10^8$ | $7.10^8$ |
| HisPyr | $8,6.10^9$ | $1,5.10^9$ | $8,9.10^8$ |
| CarPyr | $9,2.10^9$ | $1,1.10^9$ | $1,1.10^9$ |
| HcarPyr | $1,2.10^9$ | $1,4.10^9$ | $1,3.10^9$ |
| Ala | $8.10^7$ | 0 | 0 |
| Cys | $4.10^{10}$ | $1,8.10^8$ | $0,5.10^8$ |
| Lys | $3.10^8$ | 0 | 0 |
| Trp | $1,3.10^{10}$ | $7,7.10^8$ | $2,7.10^8$ |
| His | $5.10^9$ | $1,5.10^7$ | $<1.10^6$ |

Key:
[radicaux] radicals
[derives] derivates

Reaction rate constants (in $M^{-1}s^{-1}$) at pH 7 and $t^- = 25°$ C. of certain interceptors and of their parent compounds relative to oxidizing free radicals.

EXAMPLE 4

Test of the reactivity of derivates acting as a thiol with a superoxide ion ($O_2^{-1}$).

The reactivity of CysPyr and PyPyr derivates with the superoxide ion, generated by pulsed radiolysis, was determined by a conventional method. In this method, cytochrome C is used as a marker thanks to its great absorption of luminous radiation from the visible spectrum. The reduction of ferric cytochrome C by $O_2^-$· results in the appearance of an absorption band at 550 nm, characteristic of the reduced form. In the presence of another product also reacting with $O_2^-$·, the yield of reduced cytochrome C is reduced. From this data, the rate constant of the product studied with this radical-like species is deduced. By way of example, that of CysPyr is $10^5 M^{-1}s^{-1}$ while that of cysteine is only $10^4 M^{-1}s^{-1}$.

The synthesized compounds in the examples exhibit desirable properties:

They do not absorb solar UV, they offer good resistance to autooxidation of the dimethyl-2,5 pyrrol cycle. Aqueous solutions abandoned at normal temperature are perfectly stable for weeks, as indicated by monitoring these solutions with HPLC.

Peptides, amino acids, in particular Ala and His, purine and pyrimidic bases are good complexing agents of metallic ions. For example, preferably $Cu^{++}$ ions are capable of forming 1—1 complexes with Ala and His in buffered aqueous solutions at neutral pH. The reactivity of complexes with $O_2^-$ or even $^1O_2$ radicals can turn out to be desirable when it is known that certain metallic complexes, such as auranofin (an antiarthritic agent) can react with $^1O_2$, efficiently dismutate $O_2^-$ and enter into pro-oxidizing or antioxidizing redox cycles.

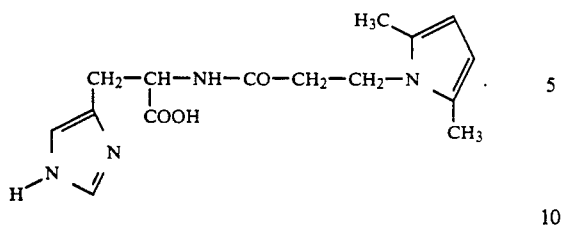

We claim:

1. A method for treating an animal having an illness in which activated species of dioxygen are involved, comprising the step of:
   administering to to said animal a pharmaceutically acceptable amount of an N-substitute pyrrole derivative having the formula:

in which:

R is an amino acid derivative, a non-protein peptide, a purine base which is substituted at position 9 by an alkyl group or a pyrimidine base possessing a free primary amino group wherein the pyrimidine base is substituted by at least one SH group; $R_1$ represents one or more substituents, identical or different, selected from the group consisting of a hydrogen and an alkyl radical containing 1 to 6 carbon atoms, or their complexes with physiologically acceptable metals wherein said N-substituted pyrrole derivative are racemates or optically active isomers with the proviso that $R_1$ is not a hydrogen when R is a derivative selected from the group consisting of glycine, leucine, phenylalanine, tyrosine, serine and glutamic acid.

2. The method according to claim 1, wherein said activated species of dioxygen is a singlet dioxygen $^1O_2$, or a free radical selected from the group consisting of $O_2^-\cdot$, OH·, AOO· and AO· in which A represents an alkyl group.

3. The method according to claim 1 wherein said activated species of dioxygen is $O_2$ and $^1O_2$.

4. The method according to claim 1, wherein R is a derivative of alanine, histidine, tryptophan, cysteine, lysine, arginine, tyrosine or mixtures thereof.

5. The method according to claim 1, wherein R is glutathione, carnosine or homocarnosine.

6. The method according to claim 1, wherein R is a adenine, guanine or cytosine.

7. The method according to claim 1, wherein $R_1$ is at positions 2 and 5 of the pyrrole ring.

8. The method according to claim 1, wherein $R_1$ is a methyl group.

9. The method according to claim 1, wherein said N-substituted pyrrole derivative is positively charged.

10. The method according to claim 1, wherein said N-substituted pyrrole derivative is negatively charged.

11. A method for intercepting an activated species of dioxygen in an animal having an illness in which activated species of dioxygen are involved, said activated species of dioxygen being selected from the group consisting of a single oxygen of ($^1O_2$) a superoxide radical ion of ($O_2^-\cdot$), a hydroxyl radical of OH·, an alkyl peroxide radical of AOO·) and an alkoxy radical of AO· wherein A represents an alkyl group comprising the step of:

delivering to to said animal, a pharmaceutically acceptable amount of an N-substituted pyrrole derivative having the formula:

in which:
R is an amino acid derivative selected from the group consisting of alanine, histidine, tryptophan, cysteine, lysine, ornithine, tyrosine and mixtures thereof; a non-protein peptide selected from the group consisting of qlutathione, carnosine and homocarnosine; a purine or pyrimidine base selected from the group consisting of adenine, guaninine and cytosine; $R_1$ represents one or more substituents, identical or different, selected from the group consisting of hydrogen and an alkyl radical containing 1 to 6 carbon atoms, or their complexes with physiologically acceptable metals wherein said N-substituted pyrrole derivatives are racemates or optically active isomers with the proviso that $R_1$ is not a hydrogen when R is a derivative selected from the group consisting of glycine, leucine, phenylalanine, tyrosine, serine and glutamic acid.

12. The method according to claim 11, wherein said N-substituted pyrrole derivative is selected from the group of formulas consisting of:

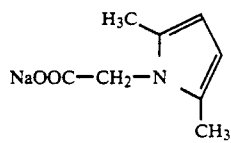

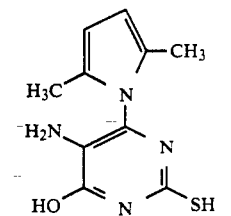

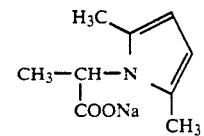

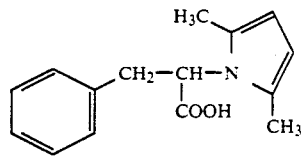

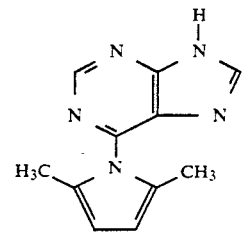

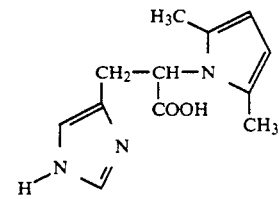

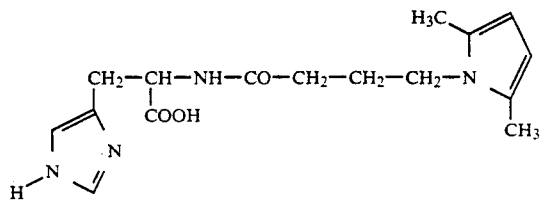

and